(12) United States Patent
Takahashi et al.

(10) Patent No.: US 7,064,813 B2
(45) Date of Patent: Jun. 20, 2006

(54) APPARATUS AND METHOD FOR MEASURING MICRO AREA IN SPECIMEN

(75) Inventors: Satoshi Takahashi, Hitachinaka (JP); Kenji Yasuda, Tokyo (JP); Yoshitada Oshida, Chigasaki (JP); Taisaku Seino, Tsuchiura (JP)

(73) Assignee: Hitachi High-Technologies Corporation, Tokyo (JP)

( * ) Notice: Subject to any disclaimer, the term of this patent is extended or adjusted under 35 U.S.C. 154(b) by 328 days.

(21) Appl. No.: 10/253,479

(22) Filed: Sep. 25, 2002

(65) Prior Publication Data
US 2003/0081209 A1     May 1, 2003

(30) Foreign Application Priority Data
Oct. 26, 2001  (JP)  ............................. 2001-328489

(51) Int. Cl.
*G01N 21/00*  (2006.01)
(52) U.S. Cl. .................. 356/73; 356/432; 356/338; 435/7.1; 435/40.5
(58) Field of Classification Search ............... 356/338, 356/496, 317, 432–436, 441, 73; 435/41, 435/7.1, 40.5; 250/461.2
See application file for complete search history.

(56) References Cited

U.S. PATENT DOCUMENTS

| | | | |
|---|---|---|---|
| 5,784,152 A * | 7/1998 | Heffelfinger et al. | ......... 356/73 |
| 6,620,625 B1 * | 9/2003 | Wolk et al. | ................. 436/180 |
| 6,784,981 B1 * | 8/2004 | Roche et al. | ................. 356/39 |
| 2002/0049682 A1 * | 4/2002 | Yamamoto et al. | ........... 705/67 |

FOREIGN PATENT DOCUMENTS

| JP | 05-098227 | * | 4/1993 |
|---|---|---|---|
| JP | 07-139701 | * | 6/1995 |
| JP | 09-303216 | * | 5/1997 |
| JP | 11-121519 | * | 4/1999 |
| JP | 2002-263318 | * | 9/2002 |

* cited by examiner

*Primary Examiner*—Layla G. Lauchman
(74) *Attorney, Agent, or Firm*—Dickstein Shapiro Morin & Oshinsky LLP

(57) ABSTRACT

Disclosed is an apparatus for measuring a micro area in a specimen in which a reagent necessary for observation and examination of a cell smear specimen or a tissue specimen is dropped to cause a reaction for a measurement and an analysis by way of an image. The apparatus includes: a micro reaction unit that is able to select a specific micro area in the specimen and to subject the specific micro area to a reaction-operation; a unit that measures; records and displays an image of the micro area; and a control unit that controls the measuring, recording, and displaying unit. Reactions can be effected quickly on such specimens as smear cell specimens and tissue slice specimens. The application of the reagent solution can be saved. A comparison between local presence of a gene or anti-body and a cell image can be made quickly and easily.

20 Claims, 2 Drawing Sheets

APPARATUS AND METHOD FOR MEASURING MICRO AREA IN SPECIMEN

BACKGROUND OF THE INVENTION

The present invention relates to a reaction-measurement apparatus for observation and examination of specimens such as cytodiagnosis or histopathological samples using a microscope etc. More particularly, this invention concerns an apparatus and method in which a reagent is made to react quickly in an area of special notice and its results can be quickly measured.

Examinations such as pathological examination and cytodiagnosis are important in examination for cancer, etc. In this kind of examination, pieces of tissue, cell, etc. are usually removed and immobilized by smearing them on the slide glass to prepare specimens. After such treatments as staining, the specimens are examined and diagnosed. Another method in which infection or abnormality is detected by allowing a cell to react with a fluorescent antibody marker or nucleic acid probe is widely used for cytodiagnosis and examination for infectious disease (Japanese Patent Laid-open No. 2000-310637, and "A Clinical Examination Special Issue <Cytodiagnosis—Prospects in the 21st century > Vol. 44, No. 11" published by IGAKU-SHOIN, LTD. Tokyo, October 2000).

A variety of staining techniques are known. Papanicolaou stain, Hematoxylin-eosin stain, Giemsa stain, etc. are used depending on the purpose. In Papanicolaou stain, for example, the cell is stained in the following procedure and used for cytodiagnosis: nuclear staining with Gill's Hematoxylin; rinsing with water and ethanol; decoloring and fractionation with alcohol hydrochloride; rinsing; coloring of nucleus with ammonia alcohol; rinsing; staining of cytoplasm; rinsing; dehydration; and penetration. An automation apparatus for staining the cell immobilized on such a slide glass has already been put on the market. An example of such an apparatus is disclosed in unexamined Japanese Patent Laid-open No. 62-27682, etc.

In recent years, in addition to the above-mentioned cytodiagnosis, there is developed a method using an oligonucleotide probe or DNA probe which hybridizes with concerned virus DNA sequence etc. of virus gene, cancer-related gene etc. to directly find whether the gene concerned is present in the tissue or cell. By using the oligonucleotide probe, DNA probe or the like in which a fluorescent substance, light-emitting substance etc., DNA probe etc. are marked, it is possible to grasp a gene present in the specimen by hybridizing and to detects it in fluorescent or light-emitting measurement, etc.

In cytodiagnosis etc., it is judged whether there are abnormalities by checking the form of cell, the size of the nucleus-cytoplasm, relations between cells.

The oligonucleotide probe, DNA probe, etc. can quantitatively detect the presence of objective genes DNA or RNA. The presence of a gene is important information in that the presence of a gene is a risk factor indicating that disease can develop. In virus infection, it can be found out before the symptoms of the disease are shown, and thus more effective treatment for the disease will become possible. Accordingly, a reliable diagnosis will be possible by combining the detection of a gene by the oligonucleotide probe or DNA probe, etc. and the measurement of the conventional cytodiagnosis.

Generally, a gene in the cell is detected through fluorescent detection by hybridizing fluorescent marker oligonucleotide probe, DNA probe, etc. Furthermore, the conventional cytodiagnosis is performed by measuring a transmitted light image after the usual staining described above. The hybridizing and the usual staining are different in procedure and are not conducted at the same time but individually.

Generally, hybridizing reaction needs a long time, several hours to one night, and therefore is poor in operability. It takes one or more hours to immune-stain a specimen on slide glass. Furthermore, a large quantity of reagent is required, since the reagent is applied all over the specimen portion on the slide glass, not on a limited or necessary portion. In particular, the reagent for hybridization reaction is costly.

SUMMARY OF THE INVENTION

It is an object of the present invention to provide an apparatus and method of subjecting specimens such as cell smear specimens to hybridization reaction or immune reaction quickly.

It is another object of the present invention to provide an apparatus and method that save a quantity of reagent to be applied.

It is still another object of the present invention to provide an apparatus and method which can obtain more detailed information in a short time by identifying a concerned area such as an abnormal cell on the basis of a usual stain image or a non-stain transmitted light image in the same specimen and conducting reaction operations including quick hybridization and immune staining for measurement of a hybridization image and an immune stain image.

The above objects are achieved by selecting a specific micro area in the specimen and providing micro reaction that which allows a reaction-operation such as hybridization for this part only.

The micro reaction mechanism may be provided with a micro nozzle mechanism that sucks and drops several pl (picoliters) to tens nl of (nanoliters) of solution. A two- or three-dimensional moving mechanism that controls the position of the nozzle mechanism and a rinsing mechanism that rinse a micro area are provided. Furthermore, a reagent storage mechanism can be provided to store reagents for reaction.

The micro nozzle mechanism section has a function of continuously or intermittently dropping the reagent on the objective area or a function of repeating dropping and sucking the reagent. This increases reaction efficiency of the reagent, shortening the reaction time. Furthermore, preparation of the reagent as a highly concentrated solution would improve the reaction efficiency and shorten the reaction time. Furthermore, the apparatus may be provided, as necessary, with a humidifying mechanism that can control the humidity at least at the micro area part or with a constant-temperature mechanism to control the temperature at least at the micro area part. The apparatus may be provided with both the humidifying mechanism and the constant-temperature mechanism. The apparatus is provided with an image measuring, recording and displaying function which measures, records and displays an image of specimen obtained after the reaction-operation by the micro reaction means, for example, a hybridization fluorescent image or light-emitting image, immune stained fluorescent image or light-emitting image etc., and an image processing function of controlling the image measuring, recording and displaying function.

Also, to achieve the above-mentioned objects, automation can be materialized by providing the apparatus with a function of measuring and recording the transmitted image of a specimen for measurement (unstained differential interference image or phase difference image, transmitted colored image of stain specimens etc.), an area selection function of determining or supporting the concerned area of which details are to be examined by extracting the features of transmitted image, and data recording function of memorizing the transmitted images in the selected area and position information.

According to an aspect of the present invention, there is provided an apparatus for measuring a micro area in a specimen in which a reagent necessary for observation and examination of a cell smear specimen or a tissue specimen is dropped to cause a reaction for a measurement and an analysis by way of an image, said apparatus comprising: micro reaction means that is able to select a specific micro area in the specimen and to subject the specific micro area to a reaction-operation; means for measuring an image of the micro area and recording and displaying the image of said micro area; and control means for controlling said measuring, recording, and displaying means.

According to another aspect of the present invention, there is provided a method for measuring a micro area in a specimen in which a reagent necessary for observation and examination of a cell smear specimen or a tissue specimen is dropped to cause a reaction for a measurement and an analysis by way of an image, said method comprising the steps of: dropping a trace amount of reagents, sequentially or simultaneously, on a plurality of designated positional spots of the specimen to wash the plurality of designated positional spots of the specimen; and measuring those images at the plurality of designated positional spots.

According to another aspect of the present invention, there is provide a method for measuring a micro area in a specimen in which a reagent necessary for observation and examination of a cell smear specimen or a tissue specimen is dropped to cause a reaction for a measurement and an analysis by way of an image, said method comprising the steps of: measuring at least part of an area of the specimen; selecting a micro area to be concerned from the transmitted images; moving the specimen on the basis of position information of said micro area to be concerned; dropping several pl to tens of nl of reagent one drop by one drop, continuously or intermittently to effect reaction; and measuring the images in said micro area part.

For the transmitted images, there may be provided a function of recording a plurality of different images with different resolutions. In particular, a high degree of analysis is possible by allowing the concerned area to have measurement images with a higher resolution together with position information in especially all the transmitted images in the specimen.

In a case where a concerned area is determined in a dialog style, a transmitted image is displayed on a monitor and a concerned position is specified by the operator. In addition, its position is recorded, and if necessary, the transmitted image at that position is measured at a higher resolution and recorded, and reaction is caused in the micro reaction mechanism and its image is recorded. It is noted that the measurement and recording of the transmitted image and the processing of the reaction by the micro reaction mechanism, the image measurement and recording may be performed continuously, or after transmitted images of a plurality of specimens are measured sequentially, the decision of the concerned area, the reaction in the micro reaction mechanism, the image measurement and recording may be made. In this case, it is desirable that the respective specimens are provided with identification means for identifying the specimens and positioning means. The identification means may be a bar code, etc. and positioning means may be a marker such as a cross that is written on a pre-determined spot of the specimen. Furthermore, there may be provided a mechanism for reading those markers. It is possible to evaluate the concerned site more in detail if transmitted images in some areas of the specimen including the micro area and image in micro areas (fluorescent image, for example) are displayed side by side or one upon another.

As described above, specimens such as smeared cell specimens can quickly be subjected to the hybridization reaction, the immune reaction, etc. It is also possible to save the amount of the reagent solution. In the same specimen, furthermore, it is possible to efficiently make measurement of hybridization images and immune stain images from measurement of usual stain images or non-stain transmitted images.

BRIEF DESCRIPTION OF THE DRAWINGS

Other objects and advantages of the invention will become apparent from the following description of embodiments with reference to the accompanying drawings in which.

DETAILED DESCRIPTION OF THE PREFERRED EMBODIMENTS

Now, an embodiment of the present invention will be described with reference to the drawings.

Figure 1:
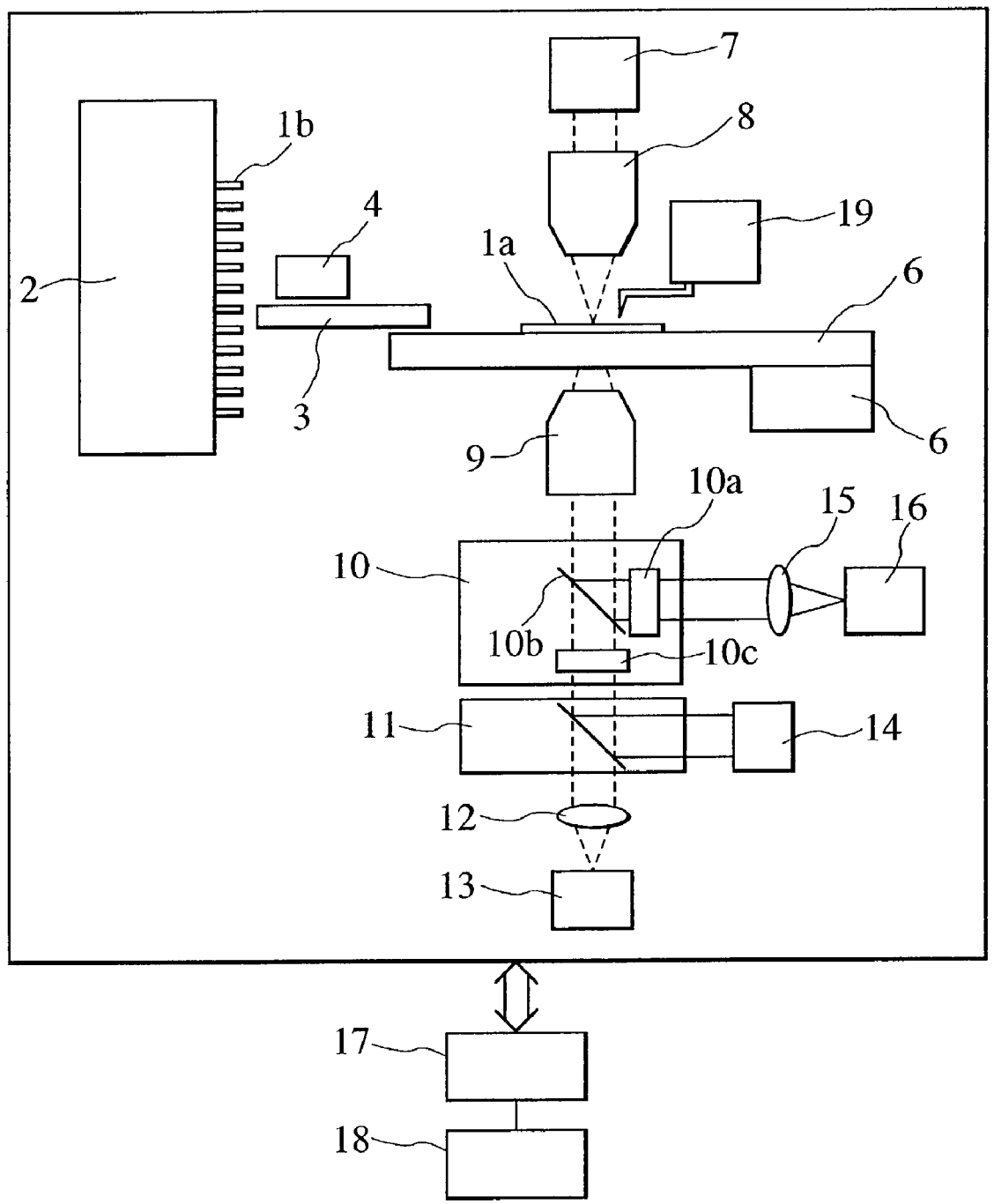
FIG. 1 is a configuration diagram of a micro area measurement apparatus according to an embodiment of the present invention.

FIG. 1 shows a configuration diagram of a micro area measurement apparatus according to the embodiment of the present invention. Tissue slices pasted on a slide glass or smeared specimens are used as specimens, which are prepared according to the known procedure such as an in situ hybridization method. Slide glasses 1a, 1b are inserted in a specimen stocker 2, and the specimen stocker 2 is mounted to the main body of the apparatus, and the plurality of inserted slide glasses are processed one after another. The slide glass 1a is carried to a measurement stage 5 by a slide glass loader 3. Then, when passing through bar cord reader 4, the slide glass is identified and the results are recorded as information on the specimen. The slide glass 1a on the measurement stage 5 can be moved by a moving mechanism 6 so that image measurement can be made all over the slide glass.

The slide glass 1a moved onto the measurement stage 5 is Koehler illuminated from above by a transmission illumination light source 7 through a condenser lens 8. The transmitted light passes through an objective lens 9, a mirror unit 10 for excitation light illumination, an optical path switchover unit 11 and a focusing lens 12 and detected by a photo-detector 13. If a two-dimensional CCD camera or the like is used as the photo-detector, an image itself is measured as a transmitted image. Generally, since the measurement field is smaller than the entire surface of the slide glass or the specimen, to obtain an image of the entire surface of the specimen, it is necessary to shift the field by the moving mechanism 6 to obtain a plurality of images and to synthesize them. In a case of using a multiplier phototube, etc. as the photodetector, it is possible to obtain an image of the entire surface of the specimen by narrowing the illumination light to a required resolution and detecting the intensity of transmitted light while two-dimensionally scanning the slide glass by the moving mechanism section 6. In this case, a color image can be obtained by taking one image after anther through a three-colored RGB filter.

In measuring transmitted light, the mirror unit 10 for excitation light illumination and the optical path switchover section 11 are transparent. Furthermore, it is possible to change the transmitted image into a differential inference image, a phase difference image, etc., and a change can be made depending on the purpose. In that case, as is known, an optical element such as a polarizing plate has to be additionally disposed in position. Measured image data are stored in a control unit 17 including a memory and a CPU, and an image synthesis or the like is performed and displayed on a monitor 18. From the image obtained, a plurality of concerned areas is picked out on the basis of parameter conditions set by the operator, and their area numbers and positions are recorded. Then, if the neighborhood of their areas is measured again at a higher resolution and high-resolution transmitted light images are recorded, more detailed analysis will be possible.

The reaction reagent containing a marker probe is dropped onto only selected, concerned areas to subject these areas to hybridization, immune staining, etc. locally. These treatments are carried out by a micro reaction mechanism 19. The micro reaction mechanism 19 is disposed above the specimen. When a reaction is operated, the transmission illumination light source 7 and the condenser lens 8 shift sideways and the micro reaction mechanism 19 moves to immediately above the specimen.

Figure 2:
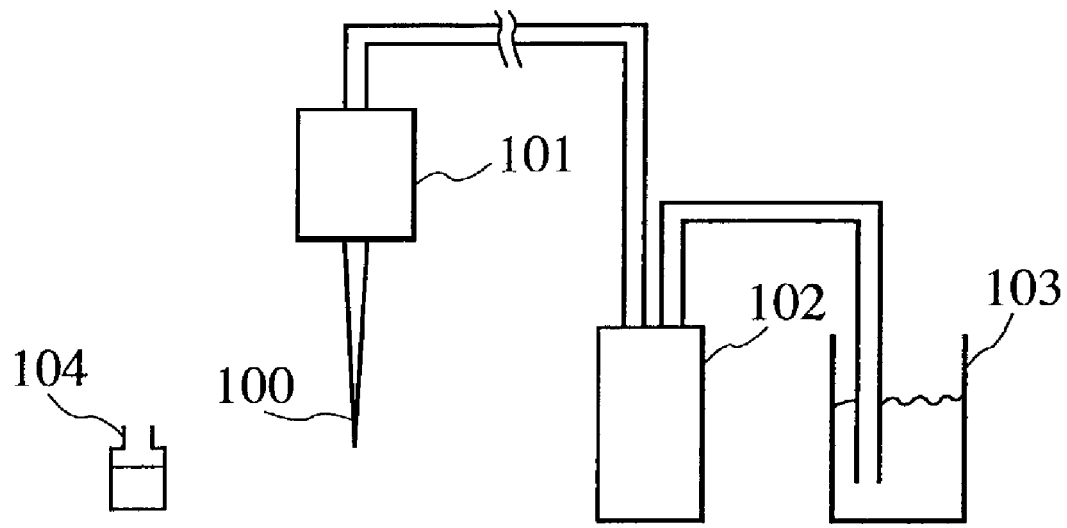
FIG. 2 is a diagram of a reagent dispensing mechanism of an embodiment of the present invention.
Figure 3:
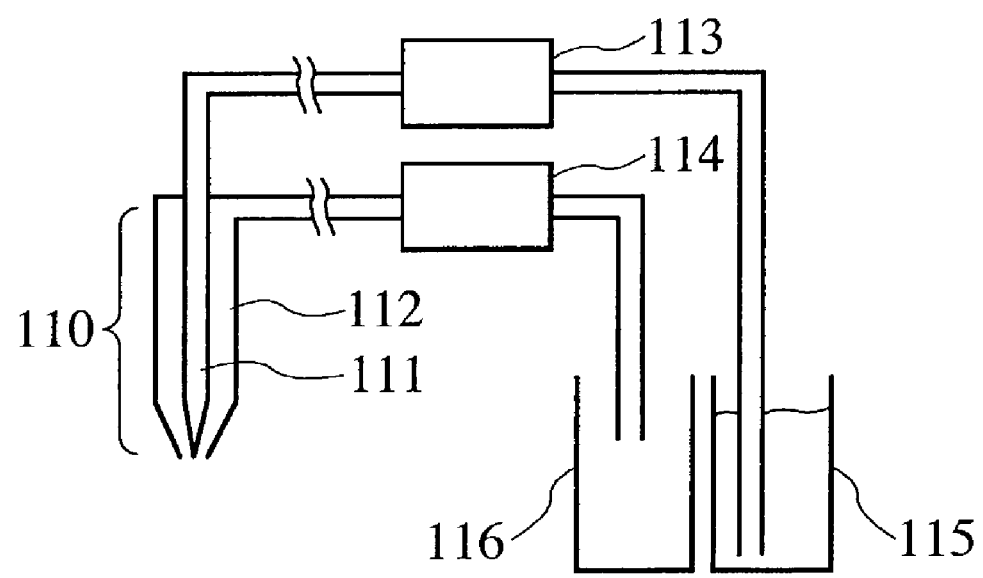
FIG. 3 is a diagram of a washing mechanism.

The micro reaction mechanism 19 is configured as shown in FIGS. 2 and 3. FIG. 2 is a configuration diagram of a reagent solution dispensing mechanism, which includes a micro nozzle unit 100 to dispense reagent solutions such as a marker probe solution, a moving mechanism 101, a syringe pump 102, a nozzle washing solution 103 and a reagent 104. FIG. 3 is a configuration diagram of a washing mechanism. A washing nozzle 110 is of a double pipe construction made up of an inner pipe 111 and an outer pipe 112, and is so constructed that a washing solution 115 is sent out from the tip of the inner pipe 111 by a solution-feeding pump 113 and is sucked from the outer pipe 112 by a suction pump 114, whereby the micro area is washed.

The moving mechanism 6 and the micro reaction mechanism 19 having a moving mechanism is so adjusted to coincide with the position of the concerned area, and then less than tens of nl of droplet is dispensed to the specimen portion in the concerned area. Generally, the reagent is dropped in an area for one to several cells, and generally several pl to tens of pl is dropped. To accelerate the reaction velocity, a highly concentrated reagent is used. This highly concentrated reagent solution is as high as several times or tens of times the known reagents generally used in concentration. To further improve the reaction efficiency, the reagent is dropped continuously or intermittently or the dropping and sucking are repeated to produce a stirring effect whereby the reaction time can be shortened. After the reaction, the reaction area is rinsed by the mechanism shown in FIG. 3. This can shorten the reaction time in the micro areas. Since the whole surface of the specimen or the slide glass is not subjected to the reaction, but the specific positions or areas to be concerned such as an abnormal cell is subjected to the reaction, the application of the reagent solution can be reduced.

After the reaction and rinsing, fluorescent images, light-emitting images, etc. are measured depending on the kind of the marker probe. In a case of a fluorescent image, light from an excitation light source 16 such as a laser source or a mercury lamp is allowed to pass through a lens 15, the mirror unit 10 for excitation light illumination and the objective lens 9 to illuminate the object area of the specimen, thereby exciting a fluorescent material and causing fluorescence to be produced. A filter unit is incorporated for fluorescent excitation and detection within the mirror unit 10 for excitation light illumination. The filter unit includes an excitation filter 10*a* that makes the light from the excitation light source monochromatic on the excitation light source side, like the usual fluorescent microscope, a dichroic mirror 10*b* that reflects excitation light and allows fluorescent light to pass therethrough, and a fluorescent filter 10*c* such as an interference filter, which further separates the fluorescent component. Fluorescence caused from the specimen is collected by the objective lens 9, and passes through the mirror unit 10 for excitation light illumination to be separated into fluorescent components. Then, the fluorescence components pass through the focusing lens 12 and are detected by the photodetector 13. The fluorescent image is measured on the basis of the predetermined resolution, a time of exposure and the size of area, and the measurements are stored.

The operations of the reaction and the measurements of the fluorescent image are repeated at times equivalent to the number of concerned areas, and the slide glasses are returned to the specimen stocker 2. These operations are automatically performed by the control unit 17 in accordance with the predetermined procedure. The above-mentioned procedure is for detection of fluorescence but in a case of the measurement of light emission, the measurement can be made in a roughly similar manner without the use of the excitation light source. It is noted that the optical path switchover unit 11 is used when the light path is switched over to an eyepiece 14 so as to visually observe the specimen.

The following information is recorded for each slide through these operations: a number attached to slides, almost all the transmitted images of the specimen, transmitted images and fluorescent images with a higher resolution at the concerned positions in the specimen, and those position information. The measurements are displayed on part of a monitor screen as a reduced image of the transmitted image on all measurement areas of the specimen along with the slide numbers. At the same time, the concerned position is placed over the display and marked. Detailed transmitted images and fluorescent images in the neighborhood of the concerned position are displayed side by side at another position on the monitor screen. Alternatively, the detailed transmitted image and fluorescent image in the neighborhood of the concerned position are synthesized and displayed as one image. This makes it possible to grasp the whole of the specimen and to observe the details, which permits effective analysis of the specimen. It is noted that the transmitted image may be an unstained transmitted image, differential interference image, phase difference image, etc. and also a colored image of the specimen stained with Papanicolaou's stain, etc. Selection of the image can be made depending on the purpose.

As set forth above, a concerned area such as an abnormal cell is identified on the basis of a usual stain image or unstained transmitted light image, reaction-operations such as quick hybridization, immune staining, etc. are carried out in that area, and a hybridization image or immune stain image is measured, whereby it is possible to obtain more detailed information quickly. In particular, position information about the fluorescent image and the transmitted light image is correctly defined, and therefore the image positional relation is clear and it is possible to compare the local presences of fluorescent DNA probes with transmitted light images such as a cell image, thus analysis can be made in more detail. Furthermore, the same results can be obtained with arrangements of the ink jet method using a piezoelectric element instead of the dispensing mechanism shown in FIG. 2. In this case, the dropping of reagent is further accelerated. In reaction-operation, the reaction is made more stable by providing a constant-temperature/constant-humidity unit above the slide glass that can control the temperature and humidity in the reaction area or placing all in a constant-temperature/constant-humidity bath. In the above-mentioned embodiment, the measurement of transmitted light images, the reaction and the measurement of fluorescent images are performed in turn for each slide glass. Instead, after the measurement of transmitted light images is made for all the slide glasses, the reaction and the measurement of fluorescent images may be effected. For this purpose, a maker for positioning is written on the slide glass specimen, and a functional section to read it is provided (not shown). Furthermore, a usual stain image or unstained transmitted light image can be obtained in the same specimen. Comparison between the local presence of gene or antibody and cell images can be made quickly with ease.

According to the present invention, it is possible to subject specimens such as smear cell specimens and tissue slice specimens to hybridization reaction, immune reaction, etc. quickly. Furthermore, since the necessary area only is subjected to the reaction, the application of the reagent can be saved.

While the invention has been described in its preferred embodiments, it is to be understood that the words which have been used are words of description rather than limitation and that changes within the purview of the appended claims may be made without departing from the true scope and spirit of the invention in its broader aspects.

What is claimed is:

1. An apparatus for measuring a micro area in a specimen in which a reagent necessary for observation and examination of a cell smear specimen or a tissue specimen is dropped to cause a reaction for a measurement and an analysis by way of an image, said apparatus comprising:
   micro reaction means that is able to select a specific micro area in the specimen and to subject the specific micro area to a reaction-operation under observation.

2. The apparatus for measuring a micro area in a specimen as defined in claim 1, wherein the micro reaction means includes a micro nozzle mechanism section for sucking and dropping several picoliters to tens of nanoliters of a solution, a two-dimensional or three-dimensional moving mechanism for controlling the position of said micro nozzle mechanism, and a washing mechanism for washing the micro area.

3. The apparatus for measuring a micro area in a specimen as defined in claim 2, wherein the micro nozzle mechanism has a function of dropping the reagent solution onto an objective micro area continuously or intermittently, or repeating the dropping and sucking.

4. The apparatus for measuring a micro area in a specimen as defined in claim 1, wherein the micro reaction means is provided with a reagent-storing function of storing a reagent for reaction.

5. The apparatus for measuring a micro area in a specimen as defined in claim 1, further comprising a humidifying mechanism that can control the humidity and/or a constant-temperature mechanism that can control the temperature at least at the micro area part of the specimen when the reaction is operated.

6. The apparatus for measuring a micro area in a specimen as defined in claim 1, wherein the specimen has a marker for individual identification and a positioning marker, said apparatus comprises means for identifying the markers and effecting positioning of the markers.

7. An apparatus for measuring a micro area in a specimen in which a reagent necessary for observation and examination of a cell smear specimen or a tissue specimen is dropped to cause a reaction for a measurement and an analysis by way of an image, said apparatus comprising:
   micro reaction means that is able to select a specific micro area in the specimen and to subject the specific micro area to a reaction-operation under observation;
   means for measuring an image of the micro area and recording and displaying the image of said micro area; and
   control means for controlling said measuring, recording, and displaying means.

8. The apparatus for measuring a micro area in a specimen as defined in claim 7, wherein the images in said micro area are fluorescent and light-emitting images.

9. The apparatus for measuring a micro area in a specimen as defined in claim 7, wherein the specimen has a marker for individual identification and a positioning marker, said apparatus comprises means for identifying the markers and effecting positioning of the markers.

10. An apparatus for measuring a micro area in a specimen in which a reagent necessary for observation and examination of a cell smear specimen or a tissue specimen is dropped to cause a reaction for a measurement and an analysis by way of an image, said apparatus comprising:
    means for measuring and recording at least a transmitted image of part of an area of a specimen;
    means for selecting a micro area to be concerned from the transmitted image;
    micro reaction means configured to effect an reaction-operation under observation in said micro area part;
    means for measuring, recording and displaying an image of said micro area part; and
    control means for said measuring, recording, and displaying means.

11. The apparatus for measuring a micro area in a specimen as defined in claim 10, wherein the transmitted images include a differential interference contrast image and a phase contrast image.

12. The apparatus for measuring a micro area in a specimen as defined in claim 11, wherein the specimen has a marker for individual identification and a positioning marker, said apparatus comprises means for identifying the markers and effecting positioning of the markers.

13. An apparatus for measuring a micro area in a specimen in which a reagent necessary for observation and examination of a cell smear specimen or a tissue specimen is dropped to cause a reaction for a measurement and an analysis by way of an image, said apparatus comprising:
    means for measuring and recording at least a transmitted image of part of an area of a specimen;
    means for selecting a micro area to be concerned from the transmitted image;
    means for recording position information on the micro area to be concerned;
    means for moving the specimen on the basis of the position information;
    micro reaction means configured to effect a reaction-operation under observation in said micro area part;
    means for measuring, recording and displaying the images in said micro area part; and control means for controlling said measuring, recording, and displaying means.

14. The apparatus for measuring a micro area in a specimen as defined in claim 13, wherein the transmitted images include a differential interference contrast image and a phase contrast image.

15. The apparatus for measuring a micro area in a specimen as defined in claim 13, wherein the specimen has a marker for individual identification and a positioning marker, said apparatus comprises means for identifying the markers and effecting positioning of the markers.

16. A method for measuring a micro area in a specimen in which a reagent necessary for observation and examination of a cell smear specimen or a tissue specimen is dropped to cause a reaction for a measurement and an analysis by way of an image, said method comprising the steps of:
 dropping a trace amount of reagents on a plurality of designated positional spots of the specimen under observation and washing the plurality of designated positional spots of the specimen, sequentially or simultaneously; and
 measuring images at the plurality of designated positional spots.

17. The method for measuring a micro area in a specimen as defined in claim 16, further comprising the step of displaying a transmitted image of part of the area of the specimen including said micro area and an image of part of said micro area one upon another or side by side.

18. A method for measuring a micro area in a specimen in which a reagent necessary for observation and examination of a cell smear specimen or a tissue specimen is dropped to cause a reaction for a measurement and an analysis by way of an image, said method comprising the steps of:
 measuring and transmitting images of at least a part of an area of the specimen;
 selecting a micro area from said at least a part of an area of the specimen to be concerned from the transmitted images;
 moving the specimen on the basis of position information of said micro area to be concerned;
 dropping several picoliters to tens of nanoliters of reagent at a time or one drop by one drop, continuously or intermittently onto said micro area to effect reaction under observation; and
 measuring images in said micro area part.

19. The method for measuring a micro area in a specimen as defined in claim 18, further comprising the step of displaying a transmitted image of part of the area of the specimen including said micro area and an image of part of said micro area one upon another or side by side.

20. An apparatus for measuring a micro area in a specimen in which a reagent necessary for observation and examination of a cell smear specimen or a tissue specimen is dropped to cause a reaction for a measurement and an analysis by way of an image, said apparatus comprising:
 a micro reaction apparatus adapted to select a specific micro area in the specimen and to subject the specific micro area to a reaction-operation, said micro reaction apparatus having a micro nozzle adapted for sucking and dropping several picoliters to tens of nanoliters of a solution, a two-dimensional or three-dimensional moving mechanism adapted for controlling a position of said micro nozzle, and a washing mechanism for washing the specific micro area.

* * * * *